US012611205B2

(12) United States Patent
Seo et al.

(10) Patent No.: US 12,611,205 B2
(45) Date of Patent: Apr. 28, 2026

(54) SURGICAL INSTRUMENT

(71) Applicant: MEERE COMPANY INC.,
Hwaseong-si (KR)

(72) Inventors: Dong Min Seo, Bucheon-si (KR); Jae Ho Cho, Incheon (KR); Yang Ho Kim, Suwon-si (KR)

(73) Assignee: MEERE COMPANY INC.,
Hwaseong-si (KR)

( * ) Notice: Subject to any disclaimer, the term of this patent is extended or adjusted under 35 U.S.C. 154(b) by 349 days.

(21) Appl. No.: 18/226,448

(22) Filed: Jul. 26, 2023

(65) Prior Publication Data

US 2024/0032904 A1 Feb. 1, 2024

(30) Foreign Application Priority Data

Jul. 26, 2022 (KR) ........................ 10-2022-0092708
Jul. 4, 2023 (KR) ........................ 10-2023-0086233

(51) Int. Cl.
*A61B 17/00* (2006.01)
(52) U.S. Cl.
CPC .................. *A61B 17/00234* (2013.01); *A61B 2017/00353* (2013.01); *A61B 2017/00982* (2013.01)

(58) Field of Classification Search
CPC ...... A61B 17/00234; A61B 17/320092; A61B 2017/00353; A61B 2017/00477; A61B 2017/00982; A61B 2017/2929; A61B 2018/00994; A61B 34/70
See application file for complete search history.

(56) References Cited

U.S. PATENT DOCUMENTS

2014/0230595 A1* 8/2014 Butt ........................ A61B 34/70
901/23
2021/0307853 A1* 10/2021 Rockrohr ................. F16C 1/12

FOREIGN PATENT DOCUMENTS

JP 2011206213 A 10/2011
JP 2015502771 A 1/2015

* cited by examiner

*Primary Examiner* — Scott Luan
(74) *Attorney, Agent, or Firm* — Dinsmore & Shohl LLP; Yongsok Choi, Esq.

(57) ABSTRACT

Provided are surgical instrument including a base body, a shaft unit extending in a direction from the base body and having an end at which an end effector is mounted, a gear unit including a first gear mounted on the base body and a second gear mounted on another end of the shaft unit and engaged with the first gear, and a bearing unit positioned between the base body and the first gear.

8 Claims, 12 Drawing Sheets

SURGICAL INSTRUMENT

CROSS-REFERENCE TO RELATED APPLICATIONS

This application is based on and claims priority under 35 U.S.C. § 119 to Korean Patent Application No. 10-2022-0092708, filed on Jul. 26, 2022, and Korean Patent Application No. 10-2023-0086233, filed on Jul. 4, 2023 in the Korean Intellectual Property Office, the disclosure of which is incorporated by reference herein in its entirety.

BACKGROUND

1. Field

The present disclosure relates to a surgical instrument.

2. Description of the Related Art

In medical terms, surgery refers to the treatment of diseases by cutting, incising, or manipulating skin, mucous membranes, or other tissues using medical devices. Particularly, open surgery, which incises and opens the skin at the surgical site and treats, molds, or removes internal organs, etc., causes problems such as bleeding, side effects, patient pain, and scarring. Therefore, recently, there has been in the spotlight as an alternative on surgery performed by forming a certain hole in the skin and inserting only medical devices, such as laparoscopes, surgical instruments, and micro-surgical microscopes, etc. or performed by a robot.

A surgical instrument is a tool for operating a surgical site by manipulating an end tool provided at the end of the shaft passing through a hole perforated in the skin through a certain driving unit manually operated by a doctor or automatically operated by a robot arm. The end tool provided in the surgical instrument performs a rotating, a gripping, a cutting, etc. by using a preset structure. However, since the parts of the driving wheel and the effector of the conventional surgical instrument are connected by a pulley wire, the structure is so complicated that manufacturing the surgical instrument is very difficult, and in addition, since there is required the wire as many as the moving degree of freedom of the effector, the shaft is required having a diameter capable of receiving the entire wire, so that there has been limitations in the conventional surgical instrument in minimizing the thickness of the instrument shaft and reducing the size of the instrument itself. In addition, the present disclosure secures a rotation angle as much as necessary to smoothly control the degree of freedom of an operation during a surgery and increases demand for a method capable of manufacturing an instrument in a simple structure.

SUMMARY

Embodiments of the present disclosure expand the driving range of the surgical instrument and reduce the width of the driving unit of the surgical instrument. In addition, the end effector may be aligned to the reference position by the surgical instrument itself. Accordingly, the surgical instrument may be miniaturized, and the driving efficiency of the surgical instrument may be maximized without loss of driving force.

Additional aspects will be set forth in part in the description which follows and, in part, will be apparent from the description, or may be learned by practice of the presented embodiments of the disclosure.

According to an aspect of the present disclosure, there is provided a surgical instrument including a base body, a shaft unit extending in a direction from the base body and having an end at which an end effector is mounted, a gear unit including a first gear mounted on the base body and a second gear mounted on another end of the shaft unit and engaged with the first gear, and a bearing unit positioned between the base body and the first gear.

In an embodiment, the bearing unit may include a first bearing mounted in an opening of the first gear and a second bearing positioned between a surface of an edge of the opening and a lower surface of the first gear.

In an embodiment, the second bearing may include a body seated in a seating groove of the first gear and a plurality of bearing rollers that is rotatably positioned on the body and in contact with the first gear and a surface of the base body.

In an embodiment, the surgical instrument may further include a first driving knob connected to the first gear.

In an embodiment, the first gear may drive the second gear to rotate in such a way that the end effector performs at least one motion of a roll, a pitch, and a yaw.

According to another aspect of the present disclosure, there is provided a surgical instrument including a base body, a shaft unit extending in a direction from the base body and having an end at which an end effector is mounted, a second driving knob including a second knob mounted on the base body and a second knob shaft connected to the second knob and having a cut-off part at which a portion of the second knob is cut off, and an alignment unit in contact with the cut-off part to align a direction of the second knob.

In an embodiment, the second driving knob may transfer a driving force to the shaft unit in such a way that the end effector mounted on the shaft unit performs at least one motion of a roll, a pitch, and a yaw.

In an embodiment, the alignment unit may include a guide bar supported by the cut-off part, a button on which the guide bar is mounted; and a resilience-forming member providing a resilience to the button.

In an embodiment, the guide bar may include a central portion curved along an outside of the button and a pair of end portions extending from opposite sides of the central portion and in contact with the cut-off part.

In an embodiment, a pair of alignment units may be provided at opposite sides of the base body.

In an embodiment, the alignment unit may include a hook fitted to the base body.

Other aspects, features, advantages other than those described above are clearly understood from the following drawings, claims, and detailed description of the present disclosure.

BRIEF DESCRIPTION OF THE DRAWINGS

The above and other aspects, features, and advantages of certain embodiments of the disclosure will be more apparent from the following description taken in conjunction with the accompanying drawings, in which.

DETAILED DESCRIPTION

Figure 1:
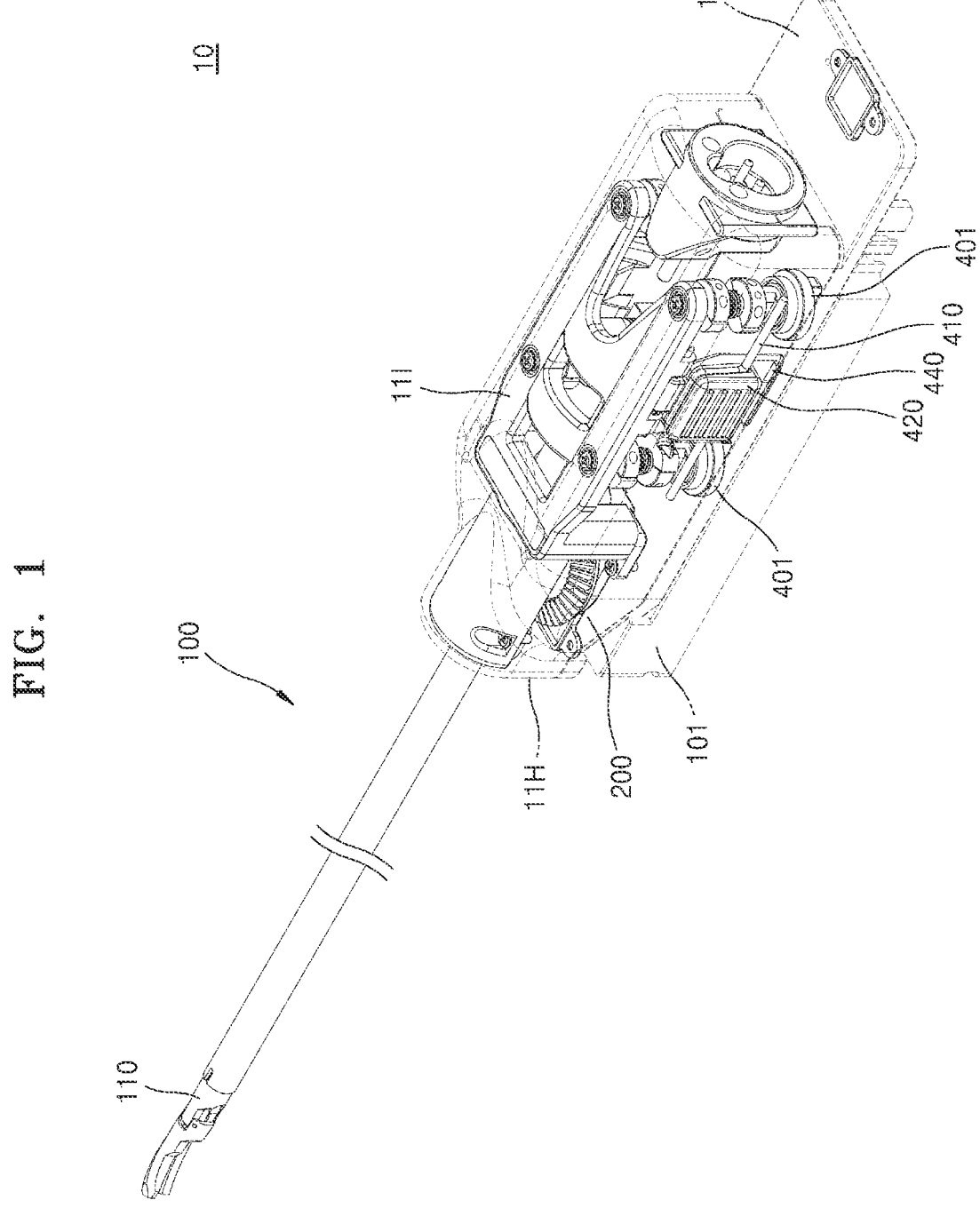
FIG. 1 is a view illustrating a surgical instrument according to an embodiment.

Reference will now be made in detail to embodiments, examples of which are illustrated in the accompanying drawings, wherein like reference numerals refer to like elements throughout. In this regard, the present embodiments may have different forms and should not be construed as being limited to the descriptions set forth herein. Accordingly, the embodiments are merely described below, by referring to the figures, to explain aspects. As used herein, the term "and/or" includes any and all combinations of one or more of the associated listed items. Expressions such as "at least one of," when preceding a list of elements, modify the entire list of elements and do not modify the individual elements of the list.

Since the present disclosure may be modified variously and may have various embodiments, some specific embodiments are illustrated in the drawings and described in detail in the detailed description. Effects and features of the present disclosure and methods of achieving the same are apparent with reference to embodiments described below in detail with reference to the drawings. However, the present disclosure is not limited to the embodiments disclosed below and may be implemented in various forms.

Hereinafter, embodiments of the present disclosure are described in detail with reference to the accompanying drawings, and the same reference numerals denote the same or corresponding elements when describing with reference to the drawings.

In the following embodiments, the singular forms may include a plurality of forms, unless the context clearly dictates otherwise.

In the following embodiments, the terms include or have mean that a feature or element described in the specification exists, and the possibility of adding one or more other features or elements is not excluded in advance.

When an embodiment is otherwise implementable, a particular process order may be performed differently from the order described. For example, the two processes described in succession may be performed substantially simultaneously or in an order opposite to the order described.

In the drawings, the size of elements may be exaggerated or reduced for convenience of description. For example, since the size and thickness of each element shown in the drawings are arbitrarily shown for convenience of description, the present disclosure is not necessarily limited to the illustrated.

The surgical instrument 10 may be used for robotic surgery or manual surgery. The surgical instrument 10 may include an end effector that is mounted on a front end portion of a surgical robot arm having an actuator and is inserted into the body of a surgical patient by the driving force from the actuator, and the surgical instrument 10 may control the end effector 110 to perform a preset operation, to thereby perform surgery.

When performing the robotic surgery using the surgical instrument 10, the surgical instrument 10 may be mounted on the front end portion of the robot arm. An electrical contact point for mediating signal transmission with the surgical instrument 10 or an actuator for transferring power may be mounted on the front end portion of the robot arm.

In addition, the surgical instrument 10 may include the end effector 110 that is mounted on an end portion thereof. The end effector 110 may be inserted into the surgical site to perform an operation required for surgery. The end effector 110 may be mounted on the surgical instrument 10 to perform at least one motion of a roll, a pitch, and a yaw. In an embodiment, the end effector 110 may include a pair of jaws for performing a grip operation. However, the configuration of the end effector 110 is not limited to those described above, and various devices for performing surgery may be provided as the end effector 110.

Figure 2:
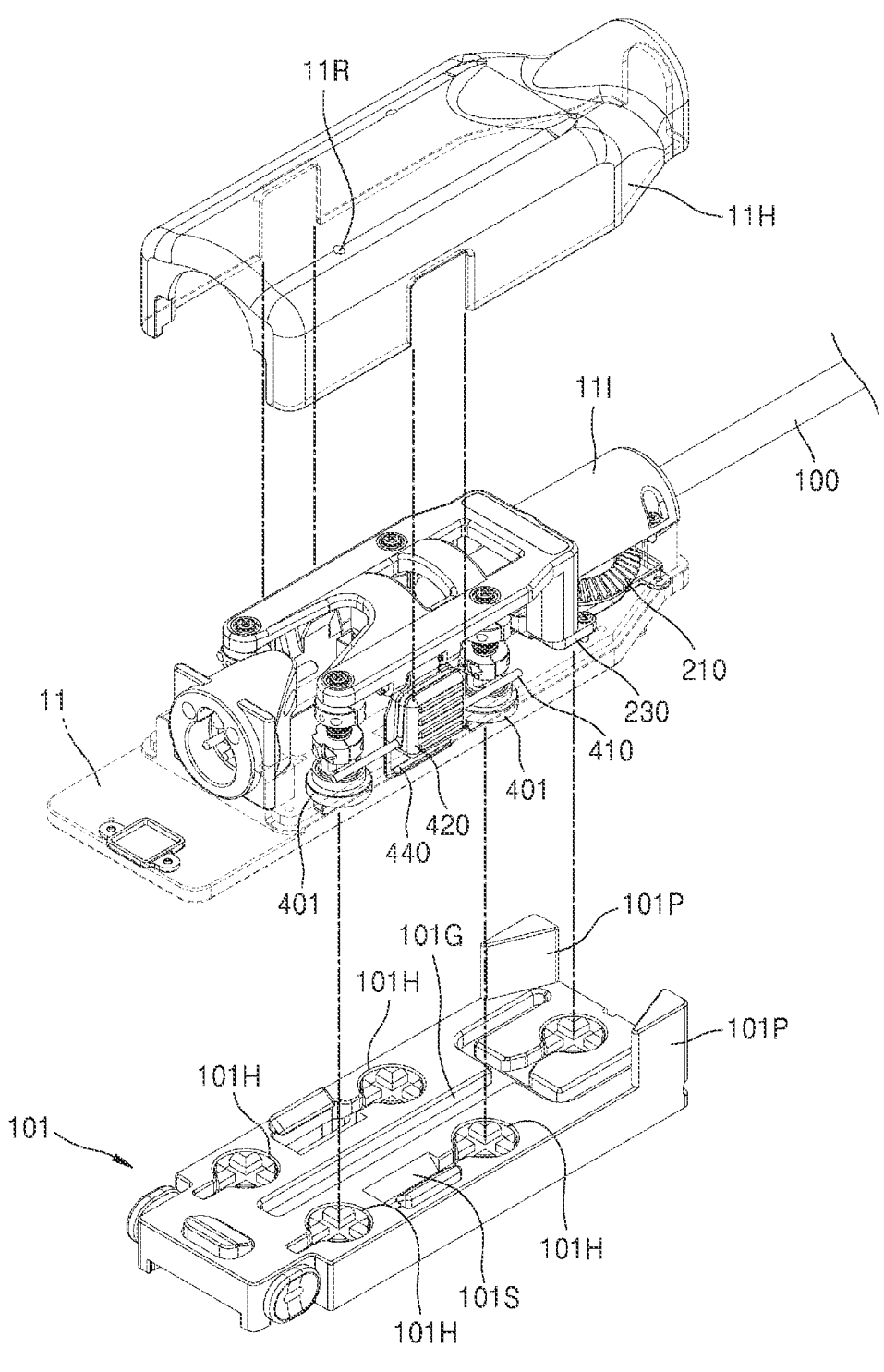
FIG. 2 is an exploded perspective view illustrating the surgical instrument according to an embodiment.
Figure 3:
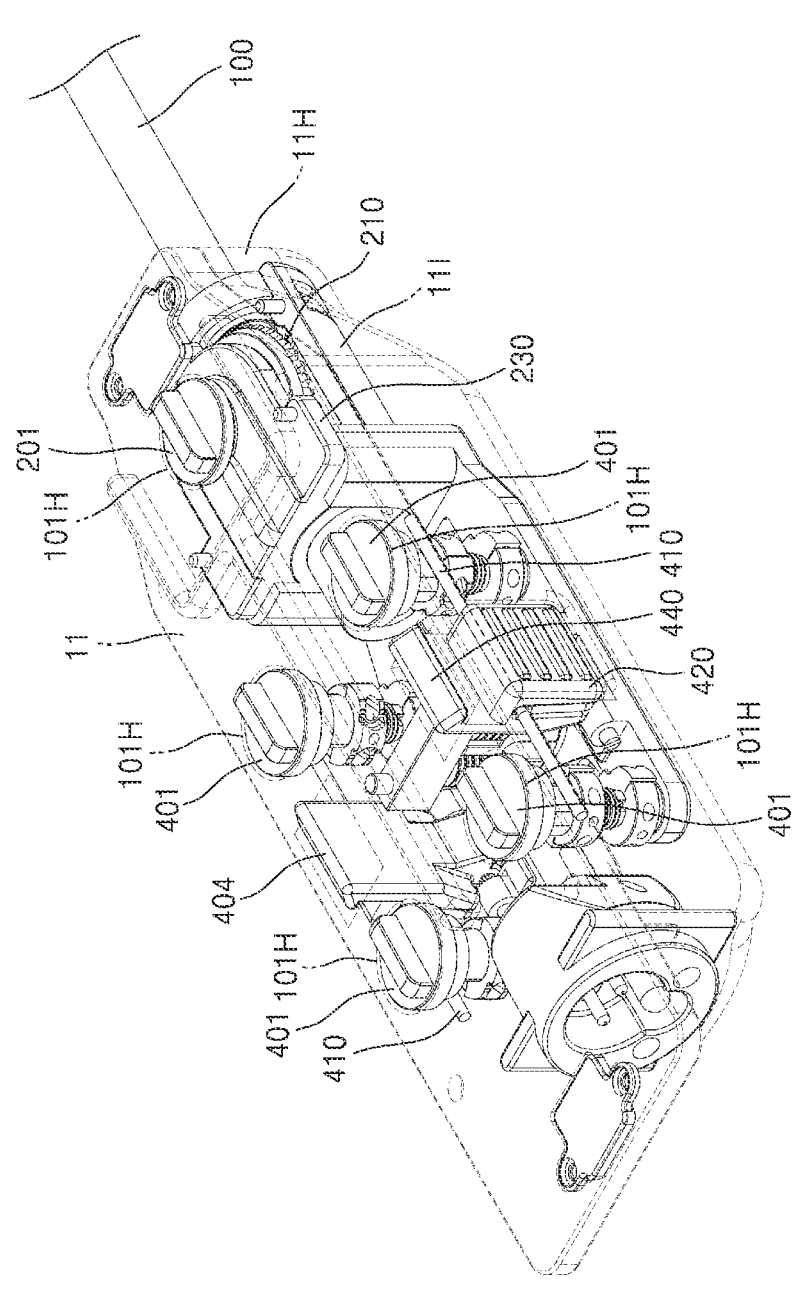
FIG. 3 is a perspective view illustrating a rear side of the surgical instrument shown in FIG. 2.

FIG. 1 is a view illustrating a surgical instrument according to an embodiment, FIG. 2 is an exploded perspective view illustrating the surgical instrument according to an embodiment, and FIG. 3 is a perspective view illustrating a rear side of the surgical instrument shown in FIG. 2.

Referring to FIGS. 1 to 3, the surgical instrument 10 may include the end effector 110 that is coupled to an end and inserted into the surgical site and a driving module that is mounted on another end opposite to the end and drives the end effector 110.

The surgical instrument 10 may include a shaft unit 100, a gear unit 200, and a bearing unit 300.

In an embodiment, the surgical instrument 10 may include a first housing 11H covering an outside, a second housing 11I covering an inside, and a base body 11. The surgical instrument 10 includes a plurality of components arranged in an inner space between the first and second housings 11H and 11I and the base body 11.

The base body 11 may be provided as a frame supporting inner components in the surgical instrument 10. Thus, the base body 11 may have a receiving space on an upper end portion, and the inner components are received in the receiving space.

The base body 11 may include at least a locking element. For example, the base body 11 may be connected to an adapter 101 that is coupled with an actuator and positioned at a lower portion of the base body 11. The base body 11 and the adapter 101 may be fitted or connected by a fastening element that penetrates the base body 11 and the adapter 101.

The surgical instrument 10 may include a mechanism for transferring the driving force to the end effector 110 or controlling the driving force. The end effector 110 may be formed at an end of the shaft unit 100 and may be inserted into the patient's body.

The shaft unit 100 may have an extended tube shape. The shaft unit 100 may extend in one direction from the base body 11, and the end effector 110 may be mounted at the end of the shaft unit 100. The shaft unit 100 may include a plurality of channels that are rotatably connected to each other. The shaft unit 100 may connect the end effector 110 to a driving source of the surgical instrument 10. The gear unit 200 may be mounted on the other end of the shaft unit 100. For example, the shaft unit 100 may include, at the other end, a shaft bearing 111 and a shaft cover 112 to which the shaft bearing 111 is fixed. The shaft bearing 111 is mounted on an end of the shaft cover 112, and the other end of the shaft cover 112 may be aligned to be in contact with a portion of the gear unit 200.

Figure 4:
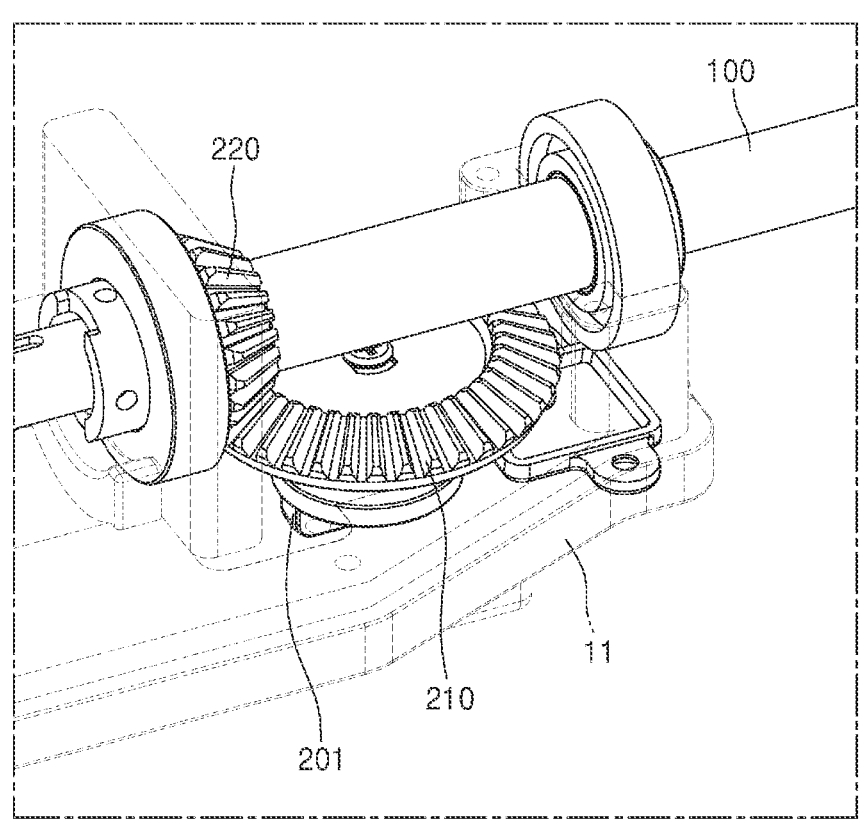
FIG. 4 is a view illustrating a gear unit of the surgical instrument in FIG. 2.
Figure 5:
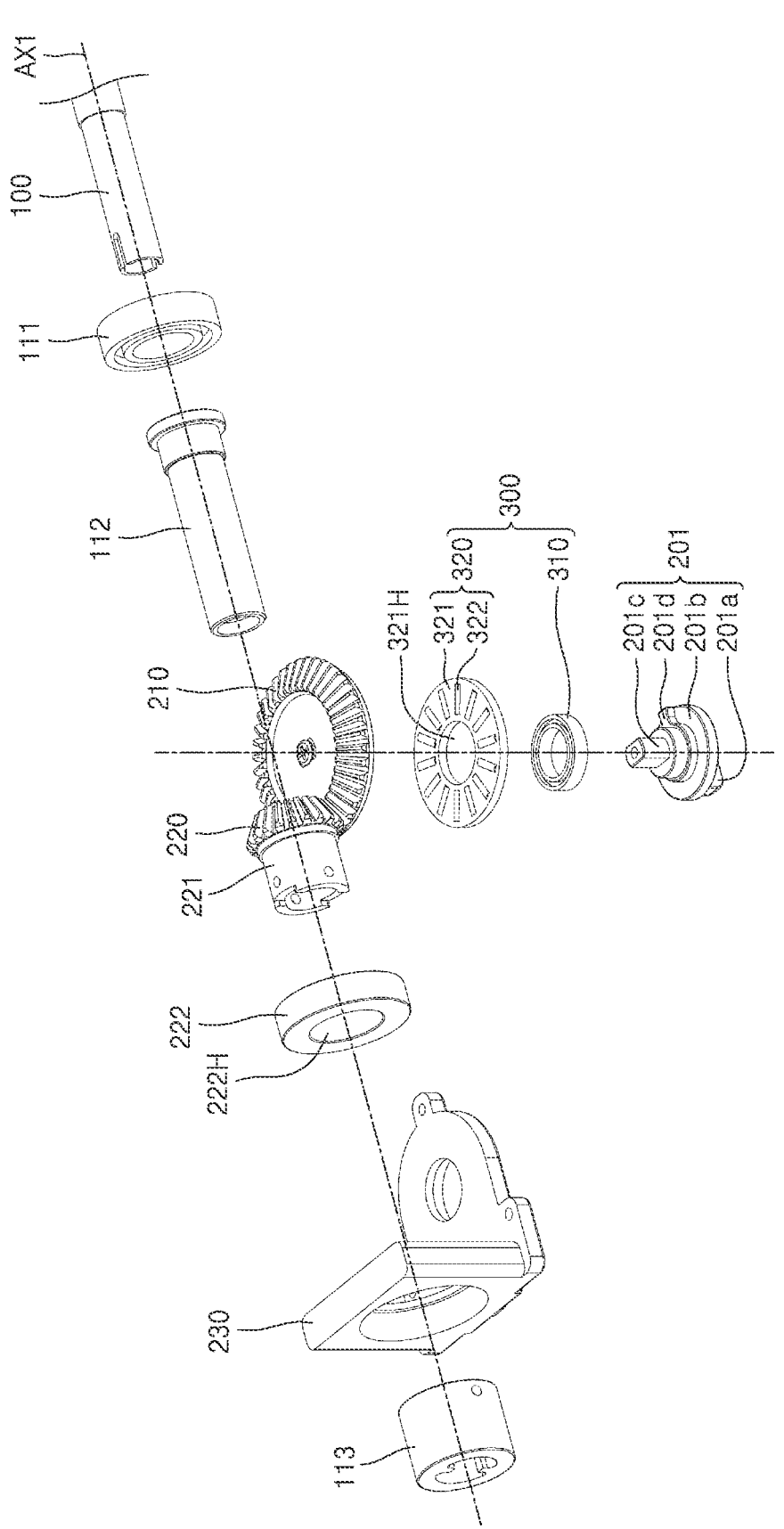
FIG. 5 is an exploded perspective view illustrating the gear unit shown in FIG. 4.
Figure 6:
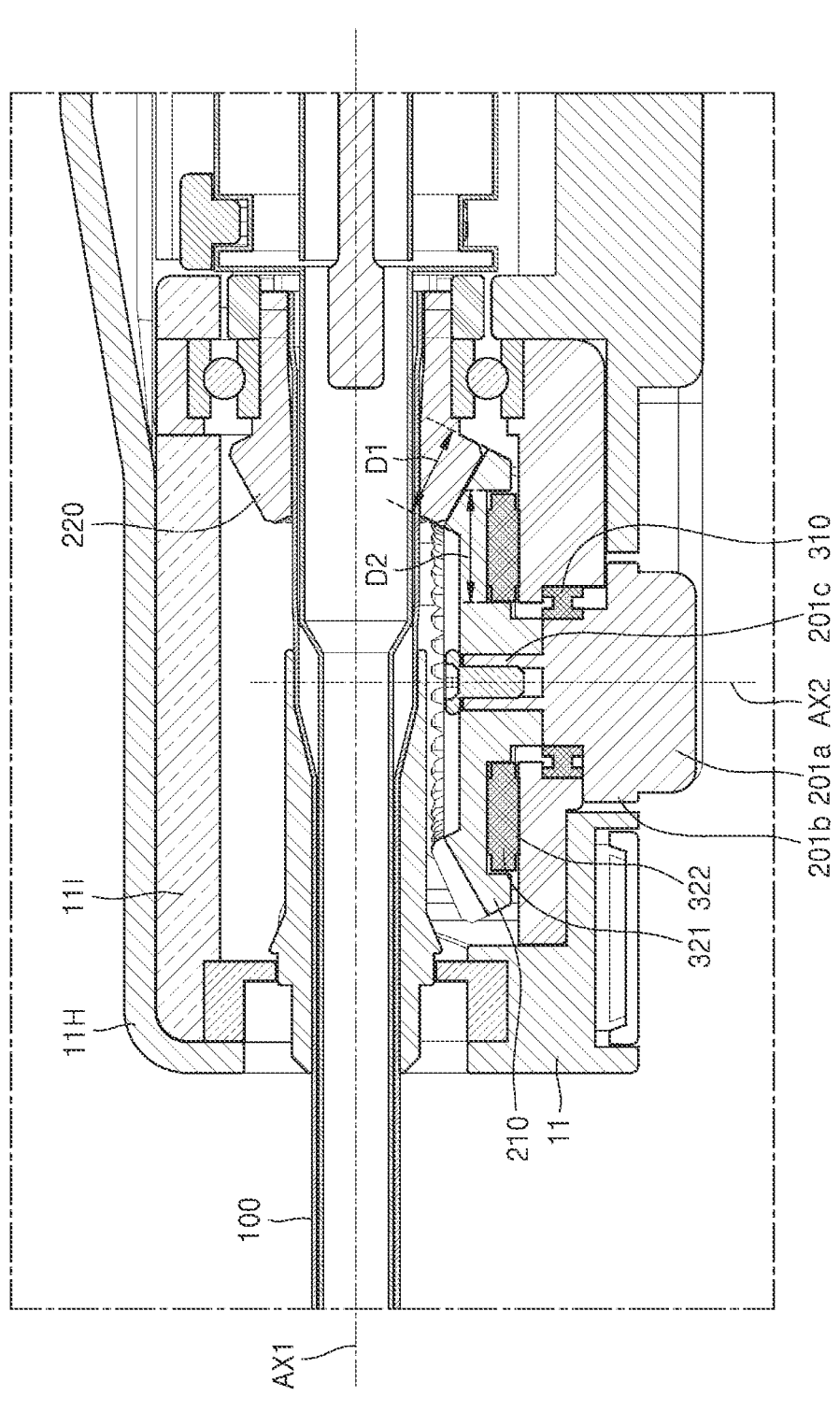
FIG. 6 is a cross-sectional view illustrating a coupled portion of the gear unit.

FIG. 4 is a view illustrating a gear unit of the surgical instrument in FIG. 2, FIG. 5 is an exploded perspective view illustrating the gear unit shown in FIG. 4, and FIG. 6 is a cross-sectional view illustrating a coupled portion of the gear unit.

Referring to FIGS. 4 to 6, the gear unit 200 may include a driving part and a driven part that crosses at a preset angle.

The gear unit 200 may include at least a gear at which the driving part and the driven part are engaged with each other. For example, the gear unit 200 of the surgical instrument 10 may include a bevel gear having a set gear ratio. However, the gear type of the gear unit 200 is not limited to the bevel gear, and various types of gear, such as a straight gear, a spiral gear, and a zerol bevel gear, may be used as the gear of the gear unit 200.

The gear unit 200 may receive power from the driving source such as the actuator that is coupled to a lower portion of the gear unit 200 and rotate and drive the shaft unit 100 and the end effector 110.

In an embodiment, the gear unit 200 may include a first gear 210, a second gear 220, and a gear frame 230.

The first gear 210 may be mounted on the base body 11. In addition, the gear frame 230 may also be mounted on the base body, and the first gear 210 and the second gear 220 may be mounted in the gear frame 230. The first gear 210 may be received in a penetrating hole of the gear frame 230 and may have a tooth shape, which is engaged with the second gear 220, on an upper surface thereof.

The first gear 210 may have a first opening 211 penetrating therethrough. The first opening 211 may protrude from a lower surface of the first gear 210 by a preset distance and be connected to a neighboring component.

A first driving knob 201 may be connected to the lower surface of the first gear 210, to thereby apply power to the first gear 210. In detail, the surgical instrument 10 may further include the first driving knob 201 connected to the first gear 210. The first driving knob 201 may be inserted into the first opening 211. The first gear 210 may be connected to the base body 11 by a plurality of fastening elements in such a configuration that the first gear 210 rotates together with the first driving knob 201.

The first gear 210 may rotate around a first shaft AX1. The first gear 210 may drive the second gear 220 to rotate in such a way that the end effector 110 performs at least one motion of a roll, a pitch, and a yaw.

The second gear 220 may be arranged at the outside the first gear 210 in a radial direction of the first gear 210. The second gear 220 may be mounted on another end of the shaft unit 100 and may be rotated around the second axis AX2 that crosses the rotation axis of the first gear 210 at a certain angle. The second gear 220 may be received in the gear frame 230 having a penetrating hole formed in a direction of the second axis AX2.

The second gear 220 may include a first connection end 221 extending by a certain distance in a direction of the second axis AX2 and be inserted into the gear frame 230. The other end of the shaft unit 100 may be inserted and connected into the first connection end 221, and a second shaft bearing 222 may be coupled to an outer surface of the first connection end 221.

At this time, the shaft unit 100 may further include a connection holder 113 into which a portion of the first connection end 221 is inserted to thereby fix the shaft unit 100 to the second gear 220. In detail, the first connection end 221 may be inserted into a connection opening 222H of the second shaft bearing 222. The first connection end 221 may be inserted out through the second shaft bearing 222, and a penetrating portion of the first connection end 221 may be inserted into the connection holder 113, so that the first connection end 221 may be fixed to the connection holder 113. Thus, the connection holder 113 may maintain a stable connection between the second gear 220 and the shaft unit 100. Accordingly, the shaft unit 100 may have at least one degree of freedom by the gear unit 200.

The bearing unit 300 may be positioned between the base body 11 and the first gear 210. The bearing unit 300 may be arranged such that the bearing unit 300 may be in contact with the lower surface of the first gear 210.

The bearing unit 300 may include a first bearing 310 and a second bearing 320.

The first bearing 310 may be positioned adjacent to a front end of the first opening 211 and the first driving knob 201 may be fitted into the first bearing 310. The first bearing 310 may be positioned between the first gear 210 and the first driving knob 201, to reduce friction generated when the first driving knob 201 rotates.

The first bearing 310 may support the first gear 210 in an axial direction or a radial direction of the first gear 210, to thereby uniformly distribute the pressure in the first gear 210. The first bearing 310 is illustrated as an example in which a commonly used ball bearing is applied, for example, but is not limited thereto, and various other types of the bearing may be applied.

The second bearing 320 may be positioned between a surface of an edge of the first opening 211 of the first gear 210 and the lower surface of the first gear 210. The second bearing 320 may include a body 321 and a bearing roller 322.

The body 321 may be seated in a seating groove provided on the lower surface of the first gear 210. In detail, the first gear 210 may have teeth and grooves, which are engaged with the second gear 220, on the upper surface, and the seating groove and the first opening 211 may be arranged on the lower surface of the first gear 210. The body 321 may be positioned to cover the open lower surface of the first gear 210 having the seating groove, so that the seating groove is covered with the body 321.

A plurality of bearing rollers 322 may be rotatably positioned on the body 321 and make contact with the surfaces of the first gear 210 and the base body 11. The bearing roller 322 may be positioned between an outer diameter and an inner diameter of the body 321 and may be protruded higher than the height or the thickness of the body 321 in a cross-sectional view. Accordingly, the second bearing 320 may be maintained in such a configuration that the body 321 is not in contact with the lower surface of the first gear 210 or with the upper surface of the gear frame 230 and is spaced apart from the first gear 210 by the bearing roller 322. Accordingly, the friction, heat generation, wearing, etc., which occur unexpectedly in rotating the first gear 210, may be sufficiently reduced or may not occur.

In addition, when the first gear 210 and the second gear 220 rotate in contact with each other, the area where the first gear 210 and the second gear 220 are engaged may overlap a portion of the bearing roller 322 of the second bearing 320.

For example, an engagement distance between the first gear 210 and the second gear 220 may be defined as a first distance D1, and a width of the second bearing 320 positioned on the lower surface of the first gear 210 may be defined as a second distance D2. The first distance D1 and the second distance D2 may have an overlapping area.

For example, the overlap area of the first distance D1 and the second distance D2 may be set to be about 50% or more of an engagement length of the second gear 220. Accordingly, when the first gear 210 and the second gear 220 are driven, since the bearing roller 322 of the second bearing 320 is supported under the area where the first gear 210 and the second gear 220 are engaged, an edge portion of the first gear 210 may be prevented from deflecting downwards, the driving force may be prevented from losing by maintaining the engagement of the first and second gears 210 and 220, and the load generated in driving may be uniformly distributed to the second bearing 320.

Referring back to FIGS. 3 and 5, the first opening 211 may have such a shape that the opening penetrates the second bearing 320 and is connected to the first driving knob 201.

The first driving knob 201 may be connected to an external actuator and control the first gear 210 to rotate. The first driving knob 201 may include a first knob 201a, a first knob body 201b, a first knob shaft 201c, and a first fixing protrusion 201d.

The first knob 201a may be connected to the actuator and receive the driving force from the actuator. The first knob 201a may rotate the first driving knob 201 clockwise or counterclockwise with respect to the second axis AX2. The first knob 201a may protrude from a surface of the first knob body 201b.

The first knob body 201b may include a first knob shaft 201c and a first fixing protrusion 201d extending in the direction of the second axis AX2 on one surface thereof. The first knob shaft 201c may be inserted into the first gear 210 and the first gear 210 and the first driving knob 201 may be integrally connected to each other, so that the first gear 210 and the first driving knob 201 may move at the same time.

Figure 7A:
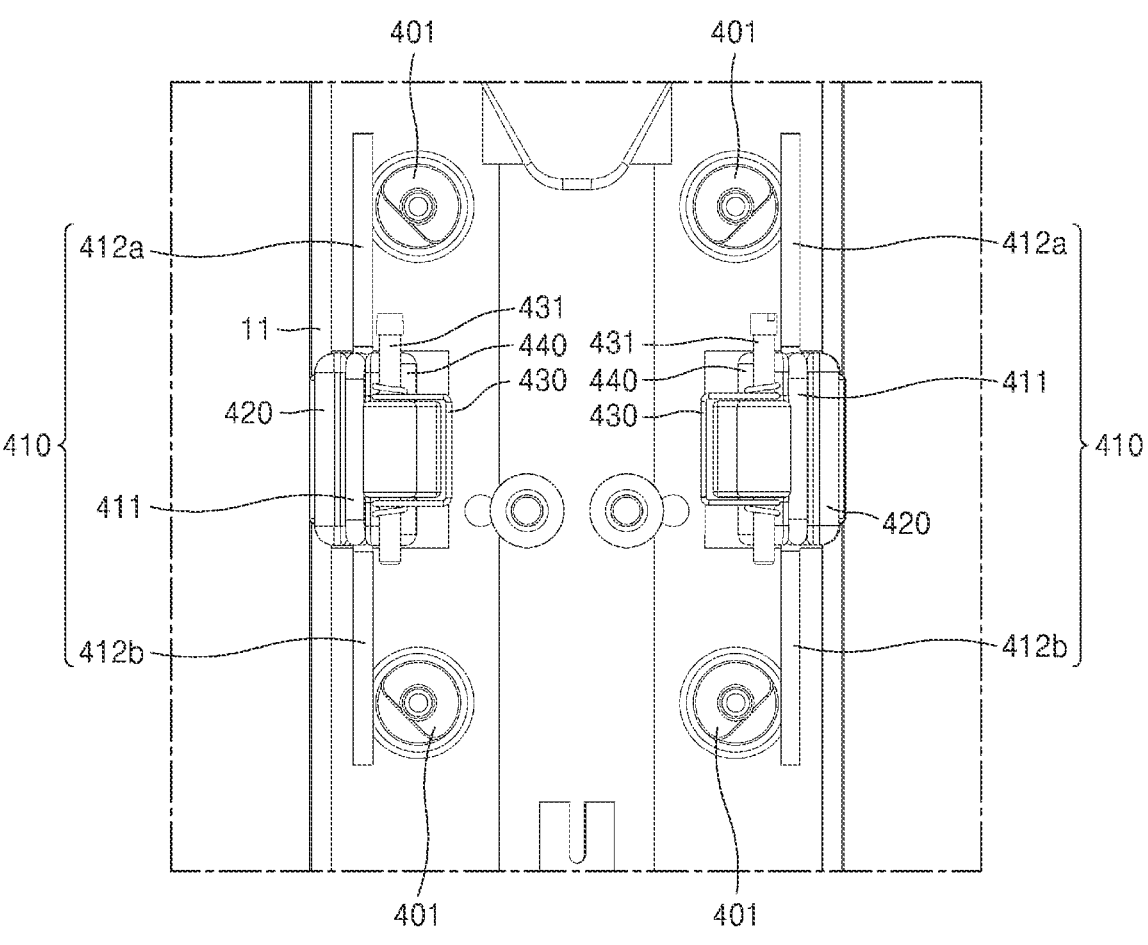
FIG. 7A is a view illustrating a state in which the surgical instrument according to an embodiment is not aligned.
Figure 7B:
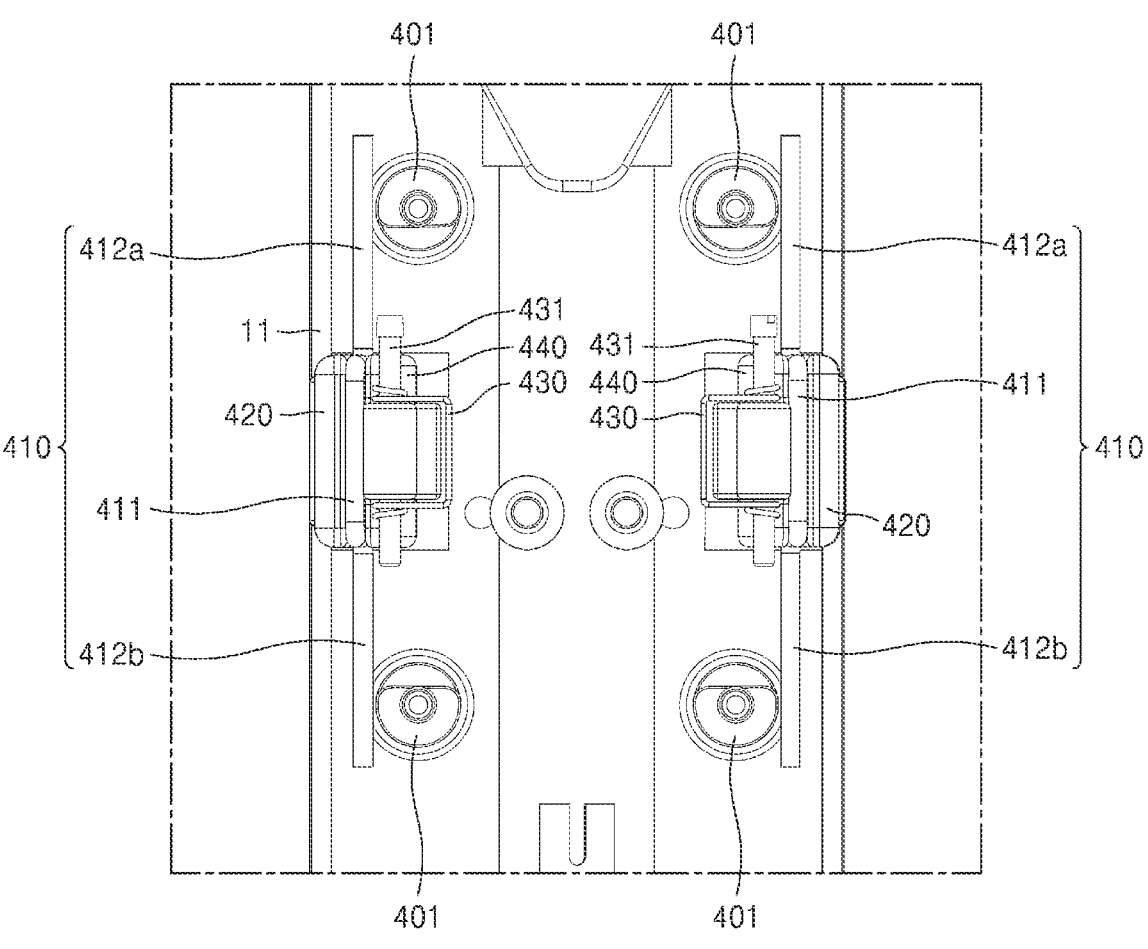
FIG. 7B is a view illustrating a state in which the surgical instrument according to an embodiment operates in safe mode.
Figure 8:
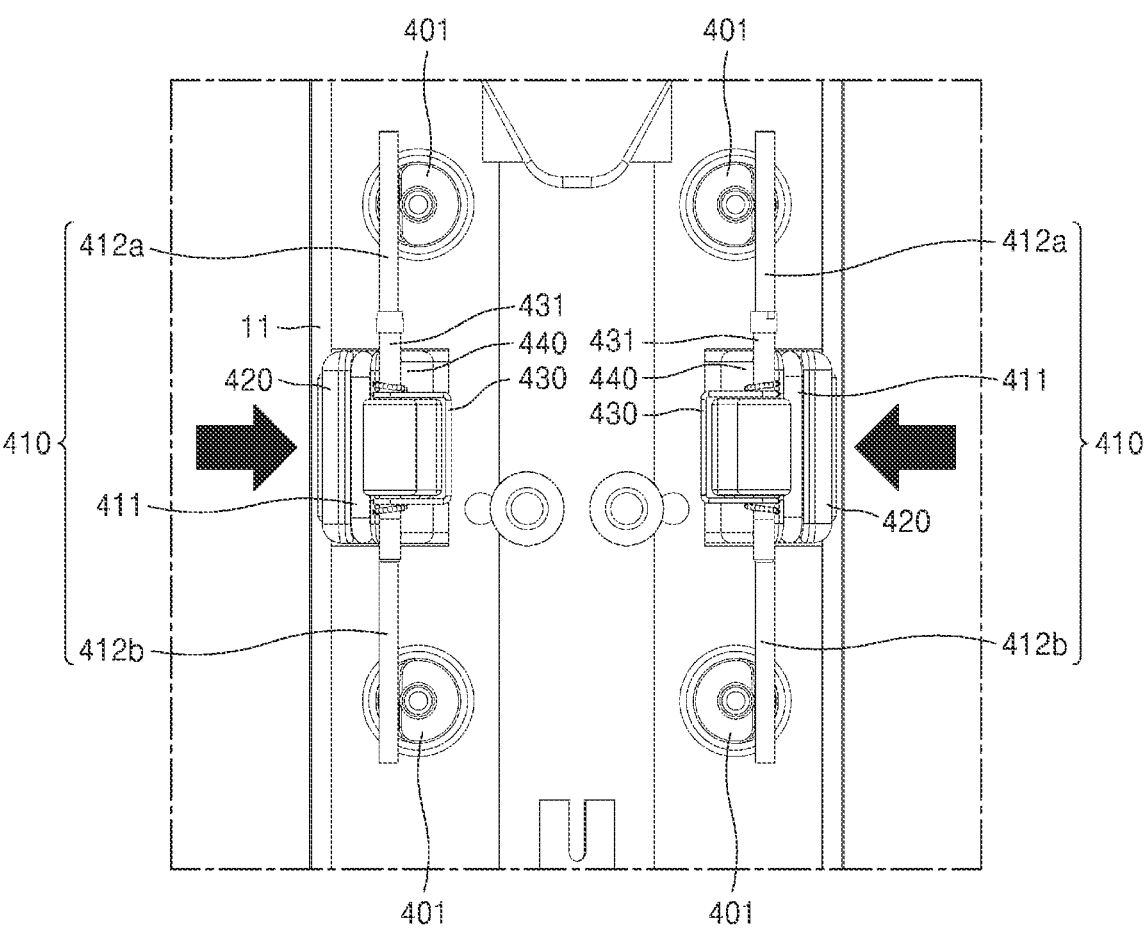
FIG. 8 is a view illustrating a state in which the surgical instrument shown in FIG. 7A is aligned.
Figure 9:
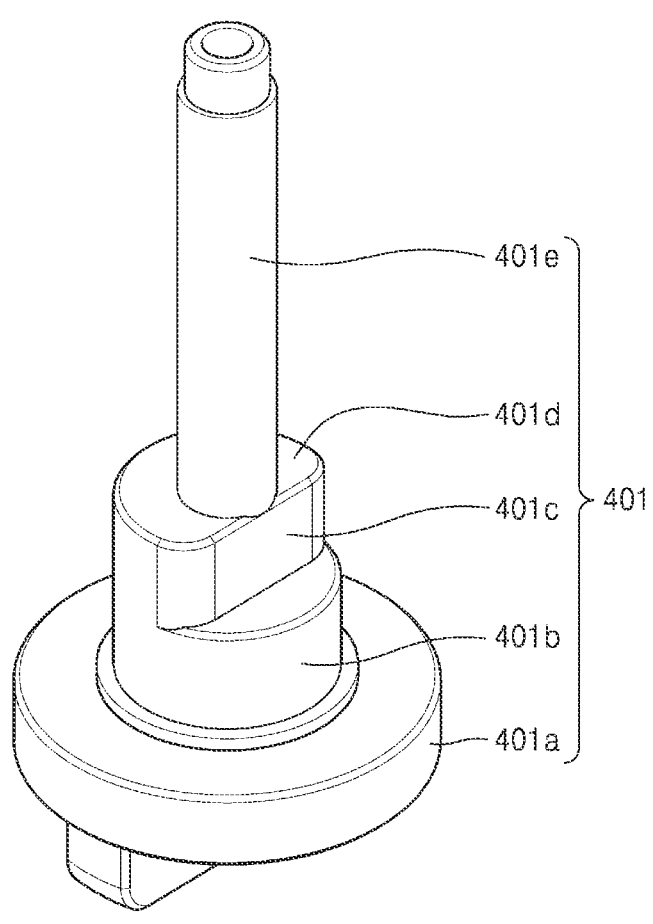
FIG. 9 is a view illustrating a second driving knob according to an embodiment.
Figure 10:
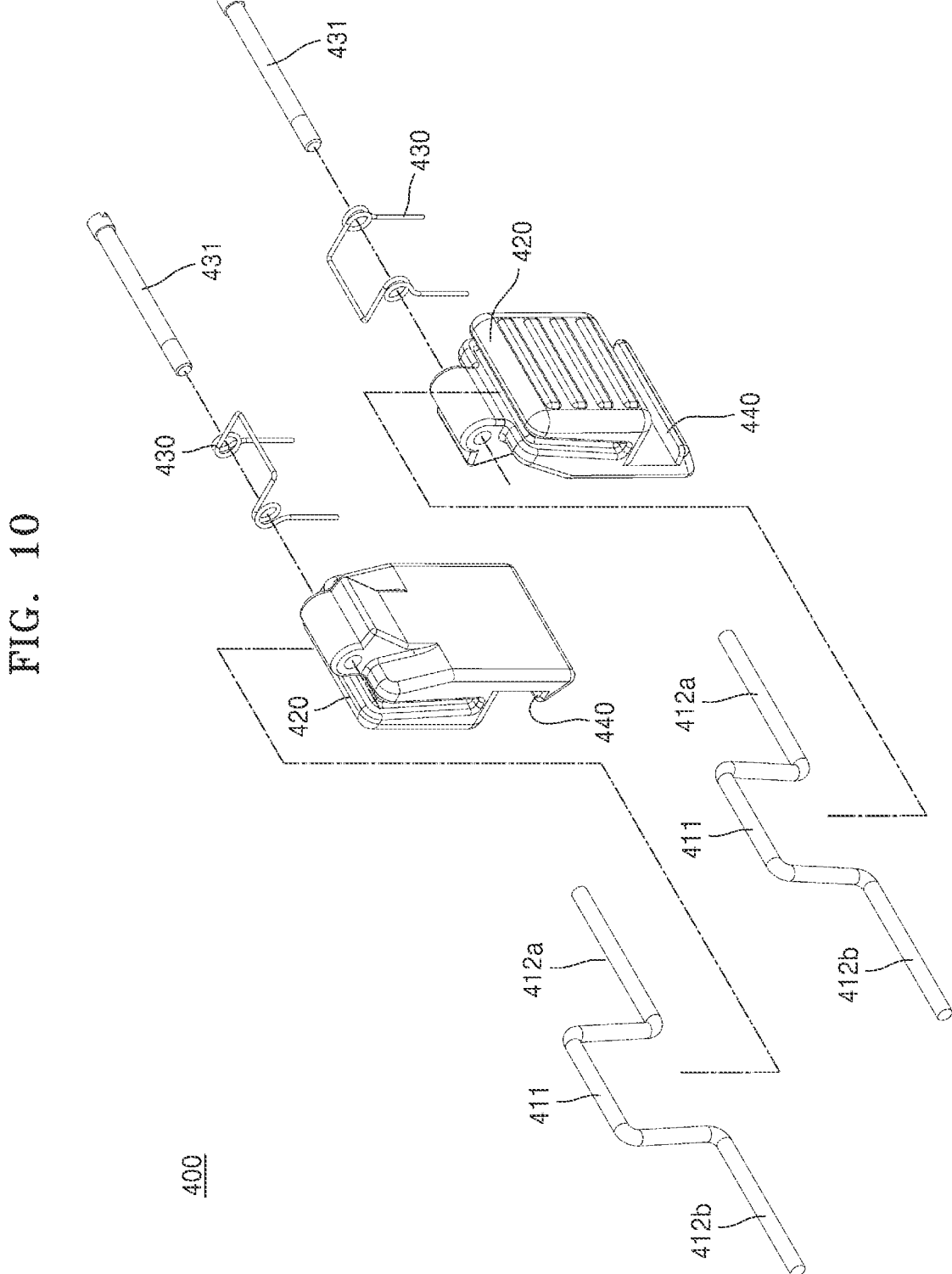
FIG. 10 is an exploded perspective view illustrating an alignment unit of the surgical instrument shown in FIG. 1.

FIG. 7A is a view illustrating a state in which the surgical instrument according to an embodiment is not aligned, FIG. 7B is a view illustrating a state in which the surgical instrument according to an embodiment operates in safe mode, FIG. 8 is a view illustrating a state in which the surgical instrument shown in FIG. 7A is aligned, FIG. 9 is a view illustrating a second driving knob according to an embodiment, and FIG. 10 is an exploded perspective view illustrating an alignment unit of the surgical instrument shown in FIG. 1.

Referring to FIGS. 7A to 10, the surgical instrument 10 may include an alignment mechanism between a medical device and an adapter 101.

In an embodiment, the surgical instrument 10 may include a shaft unit 100 having an end effector 110 at an end, a second driving knob 401, and an alignment unit 400.

When the gear unit 200 is rotated normally and reversely by the actuator, the rotational force is transferred to the second gear 220 via the first gear 210, to thereby drive the shaft unit 100 and perform various operations for surgery. In addition, the surgical instrument 10 may include the second driving knob 401 to transfer the driving force to the end effector 110. The second driving knob 401 may transfer the driving force to the shaft unit 100 to allow the end effector 110 to perform at least one motion of a roll, a pitch, and a yaw.

The second driving knob 401 may include a second knob plate 401a, a second knob body 401b, and a second knob shaft 401e. The second driving knob 401 may be positioned between the actuator and the base body 11 to transfer the driving force.

The second knob plate 401a may be mounted on the base body 11. The second knob plate 401a may include a second knob 4011a extending from a surface thereof and having a preset shape. The second knob 4011a may be connected to the actuator, and thus, the driving force of the actuator may be transferred to the second driving knob 401.

The second knob body 401b may extend from an upper surface of the second knob plate 401a. The second knob body 401b may be shaped into a stepped circular plate having at least two height steps from one surface of the second knob plate 401a.

For example, a diameter of the second knob body 401b may be smaller than that of the second knob plate 401a under the second knob body 401b. In an embodiment, a portion of the second knob body 401b may be cut off in a radial direction, and the remaining or uncut second knob body 401b may still be shaped into a cylinder having a cut-off part 401c at a side portion thereof, so that a non-rotating area in which the second driving knob 401 is prevented from rotating in a certain direction may be formed.

The cut-off part 401c may be positioned between the second knob plate 401a and the second knob shaft 401e, and the second knob body 401b may be partially cut off. The second knob shaft 401e may be connected to the second knob plate 401a and may have the cut-off part 401c that is formed by a partial cut of the second knob body 401b. The cut-off part 401c may be in contact with a guide bar 410 of the alignment unit 400, to thereby align the direction of the second knob 4011a.

The cut-off part 401c may have a flat surface, and the flat surface may have the same direction as the second knob 4011a.

The second knob shaft 401e may extend from an upper surface 401d of the cut-off part 401c. The second knob shaft 401e may be equipped with a wire (not shown) or a pulley (not shown), and, for example, when the wire is connected to the end effector 110, the end effector 110 may perform at least one motion of a roll, a pitch, and a yaw.

A pair of alignment units 400 may be provided at opposite sides of the base body 11. The alignment unit 400 may contact with the cut-off part 401c to thereby align the direction of the second knob 4011a. That is, the direction of the second knob 4011a may be aligned in a preset direction by the operation of the alignment unit 400.

The alignment unit 400 may include a guide bar 410, a button 420, and a resilience-form forming member 430. In addition, the alignment unit 400 may further include a hook 440.

Both ends of the guide bar 410 may contact with the second driving knob 401 and make the direction of the second knob 4011a be aligned with the preset direction. The guide bar 410 may be supported by the cut-off part 401c according to the grip of the button 420.

In an embodiment, the guide bar 410 may be shaped into a bending shaft of which some portion is curved. The guide bar 410 may include a central portion 411 and an end portion 412.

The central portion 411 may have a shape curved along the outside of the button 420. The central portion 411 may extend along an edge of the button 420, and thus, the guide bar 410 may be stably supported by the button 420.

The end portion 412 of the guide bar 410 may include a first end 412a and a second end 412b extending from both ends of the central portion 411 and making contact with the cut-off part 401c, respectively.

The first end 412*a* and the second end 412*b* may extend from the central portion 411 to a preset length and provide elasticity to the guide bar 410. The first end 412*a* and the second end 412*b* may support a pair of second driving knobs 401 simultaneously, and thus, the pair of second knobs 4011*a* may be aligned in the same direction.

The guide bar 410 may be mounted onto the button 420. The user may grip the surface of the button 420 to operate the guide bar 410. When the user presses the button 420, the guide bar 410 is controlled to be in contact with the cut-off part 401*c*, and when the contact pressure is applied to the cut-off part 401*c*, the second driving knob 401 rotates and the second knob 4011*a* may be aligned with a preset position.

The resilience-forming member 430 may provide a resilience to the button 420. For example, the resilience-forming member 430 may include a material having elasticity for maintaining a certain angle and a coil-type spring may be provided as the resilience-form forming member 430.

When the user releases the grip after gripping the button 420, the resilience-form forming member 430 may restore the button 420 to an initial position.

The hook 440 may be provided as a locking projection extending to the lower end of the button 420 and inserted into the base body 11, so that the hook 440 may be coupled with the base body 11. The hook 440 may be inserted into a combining groove of the base body 11 and be detachably connected with the base body 11, so that the button 420 may be fixed and coupled to the existing position even when the user grips the button 420.

The surgical instrument 10 according to an embodiment may include a structure for guiding a user to smoothly load and detach the surgical instrument 10. For example, the adapter 101 may include a slide 101S, an adapter hole 101H, a protruding block 101P, and a guide liner 101G on an upper surface thereof with which the base body 11 makes contact.

The slide 101S may be provided in a shape extending downward from the upper surface of the adapter 101 with a certain slope. Referring again to FIG. 2, when the surgical instrument 10 is coupled to the adapter 101, the hook 440 may be caught at a lower end of the locking projection of the adapter 101. The hook 440 may be constrained by a locking projection of the adapter 101 to maintain a fixed state. On the other hand, when the user presses and operates the button 420 to detach the surgical instrument 10, the tip of the hook 440 may be vertically separated and detached along the slope of the adjacent slide 101S, and the locking is released. Even in the process of installing the surgical instrument 10, the tip of the hook 440 may come into contact with the adapter 101 along the slope of the slide 101S.

A plurality of adapter holes 101H may be provided through the adapter 101, and a component for transferring the driving force of the actuator may be connected to the second driving knob 401 through the adapter holes 101H.

The protruding block 101P may protrude from the upper surface of the adapter 101 and be shaped into a block protruding to a certain height and surrounding the lower outside of the base body 11. The protruding block 101P may be formed into a locking projection in front of the surgical instrument 10 when the surgical instrument 10 is mounted.

The guide liner 101G may be provided as a groove having a certain depth on the upper surface of the adapter 101. For example, a guide protrusion (not shown), which is arranged at a lower surface of the base body 11, may be inserted into the guide liner 101G, to thereby guide the installation and detach path of the surgical instrument 10.

The protruding block 101P and the guide liner 101G may prevent the surgical instrument 10 from being separated from the adapter 101 in the process of installing the surgical instrument 10. The guide liner 101G may guide the base body 11 by which the inner components of the surgical instrument is supported to move forward and backward on the adapter 101 in a state that the base body 11 is safely seated on the adapter 101, and the protruding block 101P may be provided as a vertical wall in front of the base body 11, to thereby prevent the base body 11 from deviating from the adapter 101 a front direction.

Referring to FIGS. 3, 7A, 7B, and 8, the second knob 4011*a* may be aligned as follows by the alignment unit 400.
<Installation of Surgical Instrument>

Prior to surgery, the user may install the surgical instrument 10 on an external structure. The adapter 101 may be mounted on the external structure, and the surgical instrument 10 may be coupled to the adapter 101. When the surgical instrument is mounted on the multi-joint surgical robot, the external structure may correspond to an end portion of the multi-joint robot arm.

In this regard, the external structure may include at least an actuator to operate the surgical instrument 10, and the surgical instrument 10 may be driveably connected to the actuator so that the surgical instrument 10 may be driven by driving of the actuator. The surgical instrument 10 may include a plurality of driving knobs, and the driving knob may be connected to the actuator.

On the other hand, the end effector 110 of the surgical instrument 10 need be aligned with the initial position for the user to drive the surgical instrument 10 without errors. Accordingly, the driving knobs of the surgical instrument 10 need be changed into an alignment state by the alignment unit 400.

When the user grips the button 420 of the alignment unit 400 in a state that the direction of at least one second knob 4011*a* is not aligned, the second knob 4011*a* may be aligned in a preset direction.

The guide bar 410 may come into contact with the second driving knob 401 by the grip of the button 420, and the second knob 4011*a* may be aligned with the preset direction. Since the guide bar 410 is in contact with the cut-off part 401*c* having a flat surface, the second driving knob 401 may be rotated. Thus, the second driving knob 401 in contact with one of the first end 412*a* and the second end 412*b* may be aligned in the preset direction.

Thereafter, the surgical instrument 10 may be mounted on the adapter 101, and the second knob 4011*a* may be inserted in such a direction in which the second knob 4011*a* is aligned with the adapter hole 101H of the adapter 101. The hook 440 may be assembled to a locking projection of the adapter 101. Since the second knob 4011*a* is mounted on the adapter 101 in the aligned direction, the user may perform surgery at the reference position where the surgical instrument 10 is aligned.

In addition, the surgical instrument 10 according to an embodiment may include a mechanical alignment method and a safety mode to prevent the surgical instrument 10 from being detached in a state that the body tissue is gripped by the jaw when the surgical instrument 10 is removed in an emergency.
<Alignment of Surgical Instrument in Performing Surgery>

The user may rearrange the surgical instrument 10 in a mechanical manner in surgery. The guide bar 410 may extend in a longitudinal direction and have a certain elasticity. Even when the hook 440 is locked to the adapter 101, the second knob 4011*a* may be aligned with a preset reference position once the user grips the button 420.

Referring to FIGS. 7A and 7C, when aligning the non-aligned surgical instrument 10 with the reference position, the user may perform an alignment mode in which the non-alignment state of the surgical instrument 10 is adjusted to the alignment state by pressing the button 420 of the alignment unit 400 and a plurality of driving knobs are simultaneously aligned with the reference position. At this time, the driving knobs may be positioned in an area where the position of the cut-off part 401*c* is in contact with the first end 412*a* and the second end 412*b*, and the driving knobs may be aligned with the preset position according as the user grips the button 420.

<Safety Mode Operation of Surgical Instrument in Surgery>

Referring to FIG. 7B, the user may force the surgical instrument 10 to realign in surgery. The surgical instrument 10 may be performed in the safety mode for responding to an emergency situation occurring in surgery.

For example, the surgical instrument 10 may include a release kit to forcibly control the gripping power of the end effector 110.

The user may be in such a situation that the surgical instrument 10 has to get removed when the system is stopped or out of control in surgery. In that case, the user may adjust shaft fixing bolts of the driving knobs through an adjusting hole 11R provided at an upper end portion of the first housing 11H.

When the driving knobs rotate the fixed shaft fixing bolt in a certain direction, the operation of the end effector 110 connected to the driving knobs may be controlled. At that time, as shown in FIG. 7B, the first end 412*a* and the second end 412*b* may contact with an area that prevents rotation and is positioned on the other side of the second knob body 401*b*, and the alignment mode may not be operated. Accordingly, the user may safely remove the surgical instrument 10 even in the event of an emergency.

<Detachment of Surgical Instrument>

When the surgery is over, the second knob 4011*a* may not be aligned with the reference position despite the user's grip of the button 420 since the second knob 4011*a* and the assembled actuator are fixed.

In that case, when the user grips the button 420 with a stronger force, the hook 440 may be released from the locking projection of the adapter 101. Since the guide bar 410 has a certain elasticity, when the user grips the button 420 with a stronger force, the first end 412*a* and the second end 412*b* may move into the inside of the adapter 101 while maintaining contact with the cut-off part 401*c*, so that the hook 440 may be released from the locking projection of the adapter 101.

Thereafter, as the surgical instrument 10 is separated from the adapter 101, the second knob 4011*a* may be released from the actuator, and the direction of the second knob 4011*a* may be aligned by the force that the user grips the button 420. That is, when the user grips the alignment unit 400, the surgical instrument 10 may be separated from the adapter 101 and the direction of the second knob 4011*a* of the surgical instrument 10 may be aligned. Since the actuator is aligned with the reference position even though the surgical instrument 10 is separated from the adapter 101, the user may install a new surgical instrument in the next surgery without additional alignment of the actuator.

Figure 11:
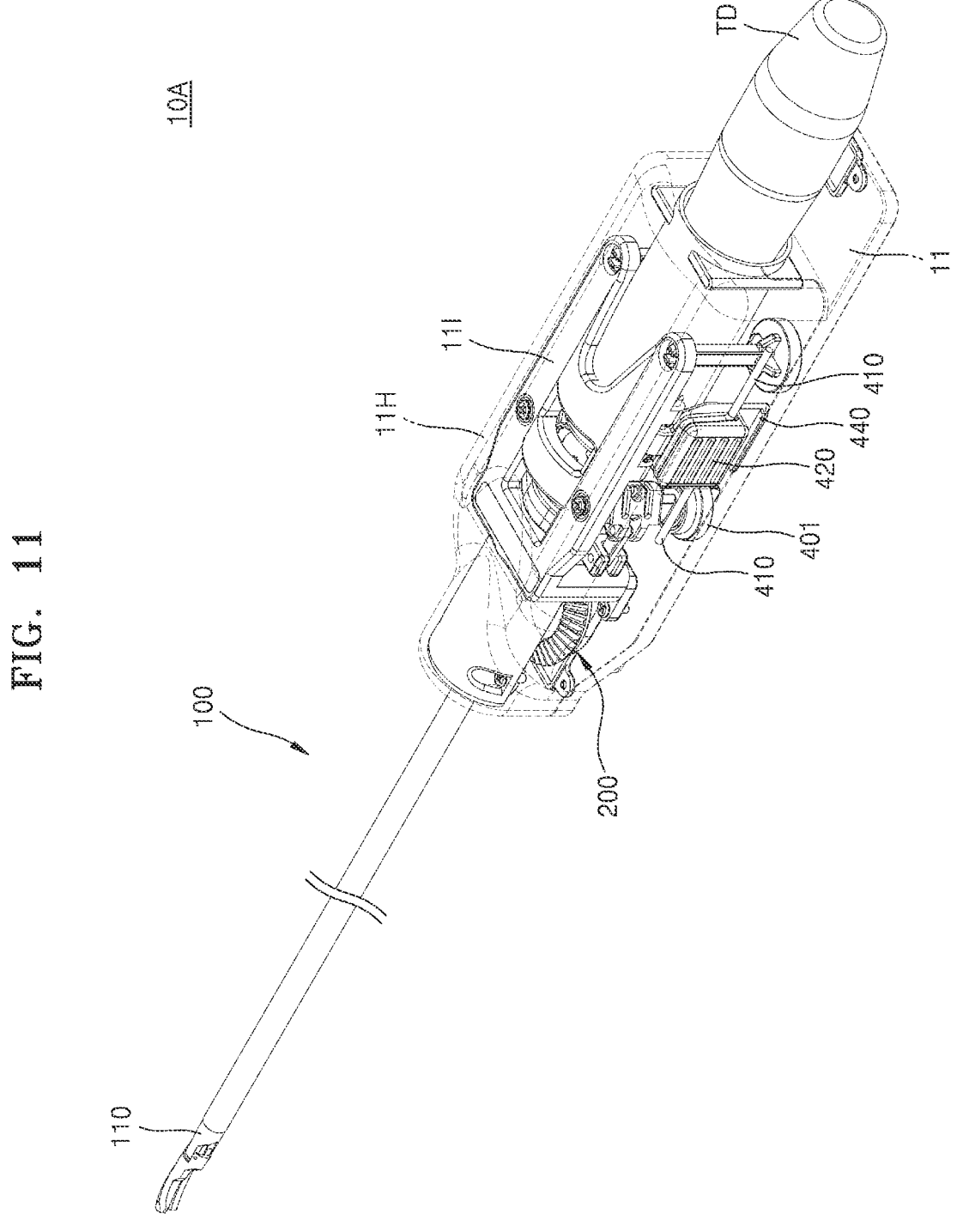
FIG. 11 is a view illustrating a surgical instrument according to another embodiment.

FIG. 11 is a view illustrating a surgical instrument according to another embodiment.

Referring to FIG. 11, the surgical instrument 10A may include a shaft unit 100, a gear unit 200, an alignment unit 400, and a transducer assembly TD.

The surgical instrument 10A may include an end effector 110 that is coupled to an end thereof and inserted into the surgical site, and an actuator that is connected to another end opposite to the end portion and drives the end effector 110.

The surgical instrument 10A may include a first housing 11H covering the outside, a second housing 11I covering the inside, and a base body 11. The surgical instrument 10A may include a plurality of components arranged in an inner space between the first and second housings 11H and 11I and the base body 11. In addition, the surgical instrument 10A may include a transducer housing 11T receiving the transducer assembly TD.

The alignment unit 400 described above may be arranged between the surgical instrument 10A and the adapter 101. The alignment unit 400 may align the direction of the second driving knob 401, and may include a guide bar 410, a button 420, and a resilience-forming member. In addition, the alignment unit 400 may further include a hook 440.

The surgical instrument 10A may include a housing into which the transducer assembly TD is inserted and may transfer electrical energy or vibration energy along a first axis AX1.

The surgical instrument 10A may transfer the electrical energy or vibration energy of the transducer assembly TD to the end effector 110, to thereby perform cauterization.

In an embodiment, the transducer assembly TD may apply electrical energy to the surgical instrument 10 to perform the cauterization operation.

In another embodiment, an internal piezoelectric device may convert power generated from the generator into ultrasonic vibration in the transducer assembly TD.

Therefore, the idea of this invention should not be limited to the embodiment described above, and not only the scope of the patent claim described below, but also all ranges changed equivalent to or equivalent to this patent claim belong to the scope of the idea of this invention.

The surgical instrument according to an embodiment of the present disclosure may transfer the driving force by the end effector having an expanded driving range and a simple structure. The surgical instrument may include a bevel gear as a means for transferring the driving force to the end effector, to thereby stably obtain the driving range. In addition, a bearing structure may be mounted on a lower portion of the gear unit, to thereby reduce unnecessary friction and uniformly distribute the load that is applied to the gear unit.

The surgical instrument according to an embodiment of the present disclosure may include the alignment unit, so that the user may easily exchange the end effector or switch the alignment state of the end effector to the existing position by a simple gripping operation in surgery. Of course, the scope of this invention is not limited to this effect.

It should be understood that embodiments described herein should be considered in a descriptive sense only and not for purposes of limitation. Descriptions of features or aspects within each embodiment should typically be considered as available for other similar features or aspects in other embodiments. While one or more embodiments have been described with reference to the figures, it will be understood by those of ordinary skill in the art that various changes in form and details may be made therein without departing from the spirit and scope as defined by the following claims.

What is claimed is:

1. A surgical instrument comprising:

a base body;

a shaft unit extending in a direction from the base body and having an end at which an end effector is mounted;

a gear unit including a first gear mounted on the base body and a second gear mounted on another end of the shaft unit and engaged with the first gear; and a bearing unit positioned between the base body and the first gear;

wherein the bearing unit includes a first bearing mounted in an opening of the first gear; and a second bearing positioned between a surface of an edge of the opening and a lower surface of the first gear;

wherein the second bearing includes a body seated in a seating groove of the first gear; and a plurality of bearing rollers that are rotatably positioned on the body and are in contact with the first gear and a surface of the base body.

2. The surgical instrument of claim 1, further comprising a first driving knob connected to the first gear.

3. The surgical instrument of claim 1, wherein the first gear rotates the second gear to allow the end effector to perform at least one motion of a roll, a pitch, and a yaw.

4. A surgical instrument comprising:

a base body;

a shaft unit extending in a direction from the base body and having an end at which an end effector is mounted;

a second driving knob including a second knob mounted on the base body and a second knob shaft connected to the second knob and having a cut-off part at which a portion of the second knob is cut off; and an alignment unit in contact with the cut-off part to align a direction of the second knob;

wherein the alignment unit includes a guide bar supported by the cut-off part;

a button on which the guide bar is mounted; and a resilience-forming member providing a resilience to the button.

5. The surgical instrument of claim 4, wherein the second driving knob transfers a driving force to the shaft unit to allow the end effector to perform at least one motion of a roll, a pitch, and a yaw.

6. The surgical instrument of claim 4, wherein the guide bar includes a central portion curved along an outside of the button; and a pair of end portions extending from opposite sides of the central portion and in contact with the cut-off part.

7. The surgical instrument of claim 4, wherein the alignment unit is provided at each of opposite sides of the base body.

8. The surgical instrument of claim 4, wherein the alignment unit includes a hook that is fitted to the base body.

* * * * *